United States Patent [19]
Bushman et al.

[11] Patent Number: 5,216,370
[45] Date of Patent: Jun. 1, 1993

[54] METHOD AND SYSTEM FOR MEASURING THE POLARIZED POTENTIAL OF A CATHODICALLY PROTECTED STRUCTURES SUBSTANTIALLY IR DROP FREE

[75] Inventors: James B. Bushman, Medina; Wayne J. Swiat, Homerville, both of Ohio

[73] Assignee: Corrpro Companies, Inc., Medina, Ohio

[21] Appl. No.: 781,896

[22] Filed: Oct. 24, 1991

[51] Int. Cl.⁵ ............................................. G01N 27/42
[52] U.S. Cl. ................................. 324/425; 204/404; 324/71.1
[58] Field of Search ............... 324/425, 71.1, 71.2, 324/700, 713; 204/404, 153.11; 307/95

[56] References Cited

U.S. PATENT DOCUMENTS

| | | |
|---|---|---|
| 3,649,492 | 3/1972 | Marsh et al. |
| 3,661,751 | 5/1972 | Wilson |
| 3,716,460 | 2/1973 | Weisstuch et al. |
| 3,730,869 | 5/1973 | Wilson |
| 3,788,962 | 1/1974 | Frenck |
| 3,824,454 | 7/1974 | Stern et al. ............ 324/457 |
| 4,001,804 | 1/1977 | Irving ..................... 340/650 |
| 4,080,565 | 3/1978 | Polak et al. |
| 4,133,734 | 1/1979 | Polak et al. |
| 4,152,228 | 5/1979 | Polak |
| 4,305,039 | 12/1981 | Steuernagel et al. ... 324/425 |
| 4,383,900 | 5/1983 | Garret ..................... 307/95 |
| 4,511,844 | 4/1985 | Tietze ..................... 324/71.1 |
| 4,823,072 | 4/1989 | Walcott et al. .......... 204/404 |
| 4,940,944 | 7/1990 | Steel et al. ............. 324/425 |

FOREIGN PATENT DOCUMENTS

| | | | |
|---|---|---|---|
| 2359413 | 5/1978 | France ............... 324/71.2 |
| 0149011 | 11/1979 | Japan ................. 324/71.2 |
| 7804164 | 10/1979 | Netherlands ....... 324/425 |
| 0744345 | 6/1980 | U.S.S.R. ............ 204/153.11 |

OTHER PUBLICATIONS

Polak, J. "Multipurpose Measuring Probe for Electrical Survey on Buried Pipelines." Third Internationl Conference on the Internal and External Protection of Pipes Sep. 1979) Paper XI, pp. 91-95. Bedford, England: BHRA Fluid Engineering.

Polak, Josef, "The Use of Multipurpose Measuring Probes to Assess the Adequacy of Cathodic Protection of Buried Pipelines." National Association of Corrosion Engineers, Aug. 1983, pp. 12-20.

Smart, Andrew L. and Nicholas, Karl W. "Cathodic Protection Potentials Without IR Drop; A New Instrument System Solves the Problem." Ohio: CORRPRO companies, Inc., Technical Paper CP-20, Mar. 1988.

*Primary Examiner*—Jack B. Harvey
*Assistant Examiner*—Maura K. Regan
*Attorney, Agent, or Firm*—Renner, Otto, Boisselle & Sklar

[57] ABSTRACT

A cathodic protection monitoring system which provides IR drop free cathodic protection potential measurements which are indicative of the effectiveness of the cathodic protection system. The system measures the polarized potential between a reference electrode and a coupon subsequent to decoupling the coupon from the protected structure. The present invention controls the time or times at which the potential is measured in order to ensure that the potential is measured only after the polarized potential has achieved a relatively steady state value. More particularly, the cathodic protection monitoring system controllably measures the polarized potential after the potential has stabilized to the extent that there are no inductive or capacitive voltage spikes present, and before the coupon potential decays significantly due to depolarization. The system also can eliminate or reduce to an acceptable level the impact of telluric and other stray DC currents in the earth or structure metal path on the potential values measured.

35 Claims, 4 Drawing Sheets

TYPICAL TIMER SEQUENCE

METHOD AND SYSTEM FOR MEASURING THE POLARIZED POTENTIAL OF A CATHODICALLY PROTECTED STRUCTURES SUBSTANTIALLY IR DROP FREE

DISCLOSURE

The present invention relates generally, as is indicated, to a cathodic protection monitoring system. More particularly, the present invention relates to a system for measuring the polarized potential of a cathodically protected metal structure substantially IR drop free.

BACKGROUND OF THE INVENTION

Cathodic protection is a known technique for controlling corrosion in a buried or submerged metal structure. Cathodic protection is utilized to protect pipelines, missile sites, or other buried or submerged structures from decay due to corrosion. However, cathodic protection systems must be monitored in order to ensure satisfactory operation and proper corrosion control. One known approach for monitoring the performance of a cathodic protection system involves measuring the electric potential between the buried or submerged structure and a reference electrode using a DC voltmeter. This procedure is sometimes referred to as measuring the cathodic protection potential of the system. Such potential measurement is indicative of the chemical activity at the interface between the metal structure and the aggressive medium, i.e., soil, water, etc. As a result, the potential measurement provides, at least in the ideal case, an indication as to the effectiveness of the cathodic protection system.

However, oftentimes the cathodic protection potential as it is measured between the structure and the reference electrode will be erroneous as a result of what is known as IR drop. IR drop is known to affect the measured potential between the structure and the reference electrode, and the resulting measured potential often misrepresents the effectiveness of the cathodic protection system. Additional detail regarding the cause of IR drop and how IR drop can complicate the measuring of cathodic protection potentials is provided in U.S. Pat. No. 4,080,565 and in the following technical papers: *Cathodic Protection Potentials Without IR Drop: A New Instrument System Solves the Problem*, Andrew L. Smart and Karl W. Nicholas, as presented at the National Association of Corrosion Engineers CORROSION-88 (March 1988) and which discusses measuring cathodic protection potentials using a pulse generator which interrupts the DC current to the structure, and *IR Drop in Cathodic Protection Measurements*, James B. Bushman, (Ohio: CORRPRO Companies, Inc., 1984). The entire disclosures of the above patent and technical papers are incorporated herein by reference.

Unfortunately, previous attempts at measuring cathodic protection potentials substantially IR drop free have resulted in erroneous measurements and/or a misrepresentation of the effectiveness of the cathodic protection system. One approach has been to measure the polarized potential between the reference electrode and an auxiliary electrode or coupon adjacent to the metal structure. However, a problem associated with measuring the polarized potential of the coupon is ensuring that the measurement is taken at an appropriate time when the polarized potential of the coupon reaches a relative steady state upon being decoupled from the metal structure.

As will be explained more fully below, it has been discovered that when the coupon is decoupled from the metal structure, the potential of the coupon undergoes rapid fluctuations, ringing, or the like, which can affect the validity of the measurement. For example, there may be inductive and/or capacitive spikes which occur in the polarized potential of the coupon following the decoupling of the coupon from the metal structure. The presence of such inductive or capacitive spikes or the like will appear in the polarized potential measurement, and, as a result, the measured potential will misrepresent the effectiveness of the cathodic protection system, as is explained more fully below. Possible factors which can contribute to inductive and/or capacitive spikes in the polarized potential of the coupon include the type, quality, and impedance of the insulation or coating on the metal structure, if any, and the impedance of the soil or other aggressive medium Furthermore, research has shown that a significant depolarization or decay can occur in the polarized potential of the coupon after decoupling, even after only approximately 100 msec or less. The charge on the coupon naturally tends to depolarize once the current is interrupted, and the measured polarized potential typically will misrepresent the effectiveness of the protection system if significant depolarization occurs. Depending on the factors which make up the overall RC time constant of the measurement system, such as the insulation of the coupon, the impedance of the soil/aggressive medium, etc., the coupon may undergo depolarization quite rapidly. In such cases, it is difficult, and often impossible, to obtain a legitimate reading using a voltmeter. The rapidly changing digital voltmeter display is difficult if not impossible to read and is subject to misinterpretation.

In view of the above-described shortcomings of existing IR drop free measurement systems for monitoring a cathodic protection system, there is a strong need in the art for a system which can provide accurate and repeatable polarized potential measurements substantially IR drop free. There is a strong need for a cathodic protection monitoring system which measures the polarized potential at predetermined and adjustable times so as to avoid the problems associated with voltage spikes or depolarization in the polarized potential of the coupon. In addition, there is a need for a system which is noise-free or virtually noise-free and which produces accurate measurements regardless of the specific test site. Furthermore, there is a strong need in the art for a cathodic protection monitoring system which is economical and portable. Such a cathodic protection monitoring system can be carried from site to site and used on different buried or submerged structures.

The use of a coupon monitoring system enables one easily to examine the coupon at any future time to determine that the criteria one is using in preventing corrosion is effective. This is far less costly than exhuming the buried structure to determine the extent of and where such corrosion is occurring.

SUMMARY OF THE INVENTION

The present invention relates to a cathodic protection monitoring system which provides IR drop free cathodic protection potential measurements which are indicative of the effectiveness of the cathodic protection system. The system measures the polarized potential between a reference electrode and a coupon subsequent to decoupling the coupon from the protected structure. The present invention controls the time or times at which the potential is measured in order to ensure that the potential is measured only after the polarized potential has achieved a relatively steady state value. More particularly, the cathodic protection monitoring system controllably measures the polarized potential after the potential has stabilized to the extent that there are no inductive or capacitive voltage spikes or the like present, and before the coupon potential decays significantly due to depolarization. The system can eliminate or reduce to an acceptable level the impact of telluric and other stray DC currents in the earth or structure metal path on the measured potential values.

The exact time or times at which the polarized potential measurement is taken after the coupon is decoupled is adjustable either automatically or by the operator. Moreover, the system may be utilized at various test sites regardless of the site location, type of structure or aggressive medium, etc. As a result, the cathodic protection monitoring system of the present invention provides accurate and repeatable cathodic protection potential measurements, and is portable and can be carried from test site to test site. Furthermore, the system is economical and easy to manufacture.

In accordance with one aspect of the present invention, provided is a method for measuring the polarized potential of a cathodically protected, submerged metal structure substantially IR drop free which includes the steps of placing and electrically coupling a metal coupon at an appropriate position with respect to the structure to the structure, providing a reference electrode positioned appropriately from the coupon and the structure, decoupling the coupon from the structure for a first determined length of time, electrically coupling the coupon and reference electrode through a voltmeter and measuring the relative voltage thereacross for a second determined length of time, such second determined length of time occurring sometime during the first determined length of time, and delaying the measuring step for a third determined length of time, commencing at the same time as the first determined length of time.

Another aspect of the present invention entails a system for measuring the polarized potential of a cathodically protected buried or submerged metal structure substantially IR drop free, comprising means for electrically coupling a metal coupon located at an appropriate position with respect to the structure, a reference electrode positioned appropriately from the coupon and the structure, decoupling means for decoupling the coupon from the structure for a first determined length of time, coupling means for coupling the coupon and reference electrode through a voltmeter and means for measuring the relative voltage thereacross for a second determined length of time, such second determined length of time occurring sometime during the first determined length of time, and delay means for delaying the measurement of the voltage for a third determined length of time commencing at the same time as the first determined length of time.

The foregoing and other objects, features, aspects and advantages of the present invention will become more apparent as the following description proceeds. It will be appreciated that while a preferred embodiment of the invention is described herein, the scope of the invention is to be determined by the claims and equivalents thereof.

To the accomplishment of the foregoing and related ends, the invention, then, comprises the features hereinafter fully described in the specification and particularly pointed out in the claims. The following description and the annexed drawings set forth in detail certain illustrative embodiments of the invention, these being indicative, however, of but a few of the various ways in which the principles of the invention may be suitably employed.

DETAILED DESCRIPTION OF THE PREFERRED EMBODIMENTS

Figure 1:
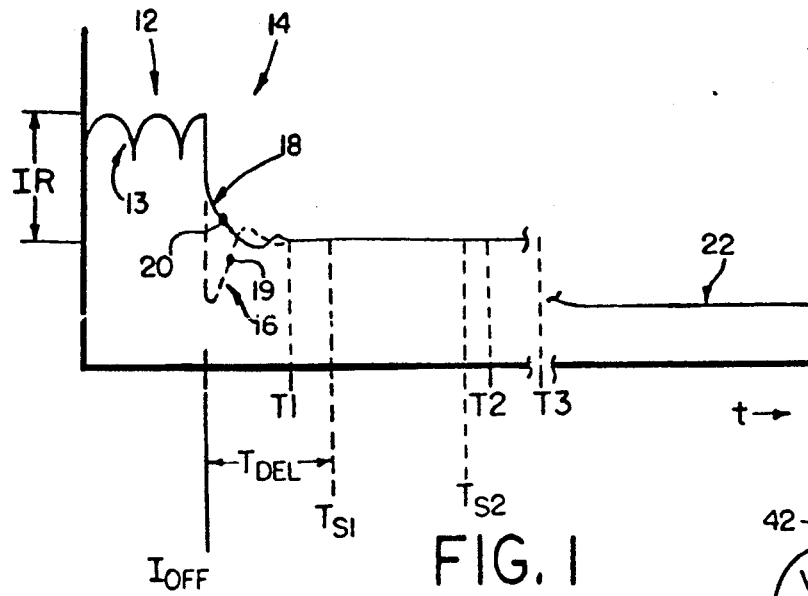
FIG. 1 is an exemplary waveform diagram of the cathodic protection potential between an exemplary coupon and reference electrode in accordance with the present invention.

Referring in detail to the drawings, wherein like reference numerals designate like parts in the several figures, and initially to FIG. 1, shown is a waveform diagram 10 showing the cathodic protection potential for an exemplary coupon used relative to a reference electrode in an IR drop free cathodic protection monitoring system. Time $I_{OFF}$ represents the time at which current to the coupon is interrupted. The cathodic protection system may be a galvanic system or an impressed current system. Segment 12 of the waveform 10 represents the potential of the coupon relative to the reference electrode during the time the coupon remains electrically coupled to the metal structure. As a result, the relative potential of the coupon prior to time $I_{OFF}$ is similar, if not identical, to that of the metal structure. It will be appreciated that a small ripple 13 may be present at the peak of the waveform segment 12 which corresponds to the AC ripple on the unfiltered rectified voltage provided by an impressed current cathodic protection system anode to the metal structure.

The segment 14 of the waveform 10 illustrates the polarized potential of the coupon relative to the reference electrode at the time immediately following time $I_{OFF}$ when the coupon is decoupled from the metal structure. As is mentioned above, at time $I_{OFF}$, the current to the coupon is interrupted and the IR portion (designated on the y-axis of FIG. 1) of the potential measurement goes to zero, as is known. Thus, segment 14 represents the polarized potential of the coupon absent IR drop.

However, the potential of the coupon has been found to undergo a rapid fluctuation upon being decoupled from the metal structure at time $I_{OFF}$. For example, such fluctuations take place, as is mentioned above, due to an inductive spike 16 (shown in phantom) or capacitive spike 18 in the potential across the coupon. As is illustrated, if the polarized potential were measured at some point in time during an inductive spike 16, for example, at point 19, the polarized potential would be uncharacteristically low and would misrepresent the effectiveness of the cathodic protection system. Similarly, if the polarized potential were to be measured during a capacitive spike, such as at point 20, the measured IR free coupon potential would be misleadingly high and also would misrepresent the effectiveness of the system.

Accordingly, it will be appreciated that it is not until approximately time T1, as shown in the waveform 10, that such spikes, or the like, have decayed substantially or diminished. At time T1, the potential of the coupon accurately reflects the polarized potential of the coupon absent any losses due to IR drop and absent the effects of spikes in the waveform due to decoupling. Time T2 represents a time shortly after time T1 and a time at which the coupon potential continues to remain at approximately the same IR drop free potential as at time T1. Thus, times T1 and T2 create a window T1-T2 in which the polarized potential of the coupon remains in a generally steady state and can be measured with appreciable accuracy. Within such window, the polarized potential is substantially free of any voltage spikes and has not yet begun to decay as a result of depolarization.

The segment 22 of the waveform 10 illustrates the polarized potential of the coupon during the period in time where the potential has decayed significantly as a result of depolarization. After approximately time T3, which may be short as 100 msec or as long as 2 to 3 seconds, or even substantially longer, the charge on the coupon will have decayed to such an extent that the measured potential will no longer accurately serve as a useful potential measurement for testing the performance of the cathodic protection system, as will be appreciated. The manner in which the precise times T1-T3 are determined is discussed more fully below.

The cathodic protection monitoring system of the present invention decouples the coupon from the metal structure at time $I_{OFF}$ and delays the measurement of the polarized potential for a short time after the coupon is decoupled from the metal structure. The monitoring system then measures the polarized potential at a time or times within the window T1-T2 where the polarized potential of the coupon will be free of spikes 16, 18, or the like. Because the polarized potential measured within the window T1-T2 has not had sufficient time to become depolarized, the measurement better represents the IR drop free polarized potential.

The polarized potential within the window T1-T2 is referred to herein as being in a relative steady state because the potential is free of any voltage spikes and has not decayed appreciably to an extent which misrepresents the effectiveness of the cathodic protection system. While it will be appreciated that the charge on the coupon ordinarily will begin to decay to some extent at time $I_{OFF}$, the decay will be negligible for at least a predetermined period of time. Those familiar in the art will appreciate that the width of window T1-T2 will be a function of the degree and magnitude of voltage spikes which occur with the coupon upon decoupling and the respective RC time constant for depolarization.

Accordingly, the monitoring system of the present invention is adjusted, either manually or automatically, to provide the appropriate delay after the coupon is decoupled from the metal structure at time $I_{OFF}$ and to measure the polarized potential of the coupon at a time within the window T1-T2 when the potential is at a relatively steady state. In a typical case such as that represented in FIG. 1, the appropiate delay between time $I_{OFF}$ and time T1 is between 2 and 3 msec in duration. The window T1-T2 usually is between 8 to 50 msec in width, again depending on the application. It also has been found that time T3 typically is up to 2 to 3 sec after time $I_{OFF}$, and after such time the polarized potential on the coupon has degraded substantially.

Figure 2:
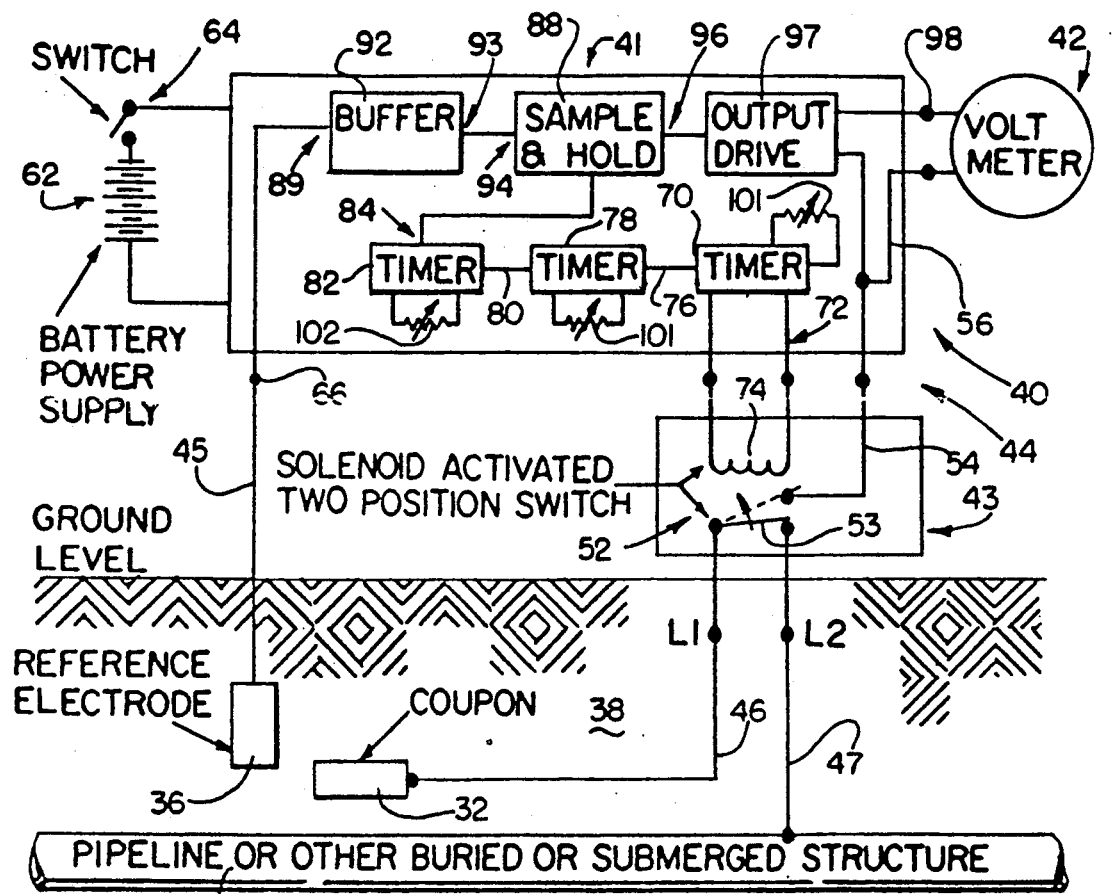
FIG. 2 is a schematic illustration of a cathodic protection monitoring system in accordance with the present invention.

The present invention has been developed to provide the above-described delays and to measure the polarized potential of a coupon so that the effectiveness of the cathodic protection system may be monitored accurately, economically, and with repeatability. Referring now to FIG. 2, a cathodic protection monitoring system 30 in accordance with the present invention is shown. The system 30 includes a coupon 32 positioned in generally close proximity to a pipeline or other buried or submerged metal structure 34. The system 30 includes a reference electrode 36 used to measure the polarized potential of the coupon 32 relative to the reference electrode. Preferably, both the coupon 32 and reference electrode 36 are buried or submerged in the aggressive medium 38 as is conventional. Moreover, the measurement may also be made with a portable reference electrode placed proximate the structure and in contact with the aggressive medium surface, i.e., the ground level 39, etc.

The system 30 includes a test module 40 which includes a timing circuit 41 and voltmeter 42. In the preferred embodiment, the test module 40 is removably electrically attached to a switch network 43 by way of terminals 44. The reference electrode 36 is electrically coupled to the test module 40 by way of an electrical cable 45. Similarly, the coupon 32 and metal structure 34 are electrically coupled to the switch network 43 using electrical cables 46 and 47, respectively.

In the preferred embodiment, the switch network 43 serves to decouple the coupon 32 from the metal structure 34 and, in turn, couples the coupon 32 to the voltmeter 42 so that the polarized potential of the coupon then can be measured. More specifically, the switch network 43 includes a normally closed, two-position switch 52 which preferably is solenoid activated. The pole of switch 52 is connected to cable 46 from the coupon 32. In its normally closed position, the switch 52 couples the coupon 32 to the metal structure 34, thus bringing the coupon 32 to the potential of the structure 34. When the switch 52 is toggled or activated in the case of a solenoid activated switch 52, the switch arm 53 decouples the coupon 32 from the metal structure 34 and couples the coupon (as shown in phantom) to line 54 which is connected to an input of the voltmeter 42 by way of line 56. The timing circuit 41 then provides a predetermined delay after the coupon is decoupled from the structure 34 and, after such delay, causes the voltmeter 42 to measure the coupon potential within the window T1-T2.

After the polarized potential is measured, the switch 52 is reverse toggled or deactivated, the switch arm 53 returns to its normally closed position, thereby recoupling the coupon 32 to the metal structure 34. As will be appreciated, the exact switching times of the switch 52 are controlled by the timing circuit 41, and it is the timing circuit which provides the desired delays when making a measurement, as is discussed more fully below. The test module 40 is powered by a battery 62 or other power supply and is activated by initialization switch 64.

The test module 40 preferably is portable, and the operator can carry the test module to various test sites in order to monitor the cathodic protection system. A switch network 43 is located preferably at each test site where it is desirable to measure the cathodic protection potential substantially IR drop free. The switch network is connected to the electrical cables 46, 47 which extend from within the aggressive medium 38. Accordingly, the test module 40 can be removably attached to the switch network 43 at each test site by way of terminals 44. This permits the operator to simply plug the portable test module 40 into the switch network 43 in order to take one or more measurements. The test module 40 then can be unplugged and used to take another measurement at a different site. In an alternate embodiment, the test module 40 and switch network 43 from a single integrated component which may be carried to each test site. In such case, the operator has to connect the cables 46 and 47 to the switch network 43 prior to taking a measurement at each site. In another embodiment, both the test module 40 and switch network 43 can be installed at each test site.

Preferably, the switch network 43 is solenoid activated and is encapsulated and/or potted with silicone rubber or the like in order to protect the electrical components therein from dirt, sand, water, etc. The voltmeter 42 preferably is of the digital variety, although an analog voltmeter will suffice. Examples of a voltmeter 42 suitable for use in accordance with the present invention include the commercially available Beckman Model No. HD110 and Fluke Model No. 77.

The reference electrode 36 may be made of Cu—CuSO$_4$ or any other known suitable material. The reference electrode 36 may be portable and is carried with the test module 40 to each respective test site. The reference electrode 36 is then placed in contact with the ground or other aggressive medium 38 at the appropriate location. Preferably, a reference electrode 36 remains buried or submerged within the medium 38 at each respective site. In such an embodiment, the electrical cable 45 is connected to the test module 40 at terminal 66, as shown.

Describing in detail the operation of the present invention, the coupon 32 initially is coupled to the metal structure 34 by way of the switch network 43, as is described above. The operator begins the measurement by closing the initialization switch 64 thereby electrically coupling the battery 62 to the test module 40 which, in turn, initiates the timing circuit 41. More specifically, by closing the switch 64 or by utilizing an equivalent trigger circuit to initiate the measurement procedure, a decoupling timer 70 is triggered, and its output 72 goes high or changes state for a prescribed period of time. During such time, the output 72 energizes the coil 74 of the solenoid in the switch network 43. As a result, the switch 52 decouples the coupon 32 from the metal structure 34 at a time represented by $I_{OFF}$ (FIG. 1) and during such energized period, connects the coupon 32 to the input 56 of the voltmeter 42.

When the decoupling timer 70 is triggered and its output 72 is energized, i.e., at time $I_{OFF}$, the secondary output 76 of the decoupling timer 70 also changes state, thereby triggering the delay timer 78. It is the delay timer 78 which delays the measuring of the coupon potential until the coupon potential is free of inductive or capacitive voltage spikes or the like. More particularly, the delay timer 78 is used to provide a predetermined delay time $T_{DEL}$ (FIG. 1) between the time $I_{OFF}$ (when the coupon 32 is decoupled from the metal structure 34) and time $T_{S1}$ which is predetermined to occur within the window T1-T2. The delay time $T_{DEL}$ is of a predetermined duration in order that the delay time $T_{DEL}$ expires at a time within the window T1-T2 where it has been determined that the polarized potential on the coupon 32 will have achieved a relative steady state.

Once the delay timer 78 completes its timing cycle at time $T_{S1}$, the delay timer output 80 changes state and, in turn, triggers sampling timer 82. The output 84 of the sampling timer 82 defines a sampling window $T_{S1}$-$T_{S2}$ within the window T1-T2, as is described below. It is within this sampling window $T_{S1}$-$T_{S2}$ that the steady state polarized potential of the coupon 32 preferably is measured by the system 30. When the sampling timer 82 is triggered, its output 84 changes state for a predetermined amount of time along line 86 and thereby enables the sample and hold (S/H) circuit 88 which is used then to measure the coupon 32 potential. In the preferred embodiment, the output 84 returns to its original state sometime prior to a time T2 which, as is noted above, represents a time at which the coupon potential still is at a relatively steady state. Once the sampling timer 82 times out, the output 84 returns to its original state and the S/H circuit 88 becomes disabled, thereby preventing erroneous measurements from occurring outside of the window T1-T2.

Referring now to the specific manner in which the coupon potential is measured while the S/H circuit is enabled, the reference electrode 36 is coupled by way of cable 45 to the input 89 of buffer 92. The buffer 92 in the preferred embodiment serves to minimize any current flow between the reference electrode 36 and the coupon 32. The buffer output 93 is coupled to the input 94 of the S/H circuit 88, and the S/H circuit 88 utilizes known sampling techniques to sample the coupon potential relative to the reference electrode. As is noted above, such measurement of the coupon potential will only occur within the sampling window $T_{S1}$-$T_{S2}$ when the S/H circuit 88 is enabled.

The output 96 of the S/H circuit 88 serves as the input to the output drive 97. The output of the output drive 97 is coupled to the input 98 of the voltmeter 42 such that the relative potential between the reference electrode and the coupon can be measured and/or displayed by the voltmeter 42. The operator simply records the measurement as viewed from the voltmeter or, alternatively, the measurement(s) can be stored electronically in an optional RAM (not shown).

After the coupon potential is measured and the sampling timer 82 has timed out, the output 84 of the sampling timer changes back to its original state, thereby disabling the S/H circuit 88, as noted above. Some predetermined time thereafter, the decoupling timer 70 times out such that its output 70 returns to its de-energized state. As a result, the solenoid coil 74 is deactivated and the switch arm 53 returns to its normally closed position. Thereafter, the coupon 32 again charges to the potential of the metal structure 34 such that the two are at the same, or approximately the same, potential. If desired, the measurement procedure is then repeated.

In the preferred embodiment, the sampling rate of the S/H circuit 88 is a multiple of sixty hertz (60 Hz) or other standard frequency. Typically, the cathodic protection system is powered by a sixty hertz (60 Hz) AC power line. As a result, the noise associated with a sixty hertz (60 Hz) signal, including any harmonics, can be substantially eliminated. While sixty hertz (60 Hz) is a standard frequency in the United States, fifty hertz (50 Hz) prevails in Europe, and other standards are used in other countries. In another embodiment, different sampling rates may be used. Furthermore, various filters such as an AC filter can be utilized, if desired. Moreover, the polarized potential need only be sampled once during a given measurement rather than obtaining the potential based on several samples.

Figure 3:
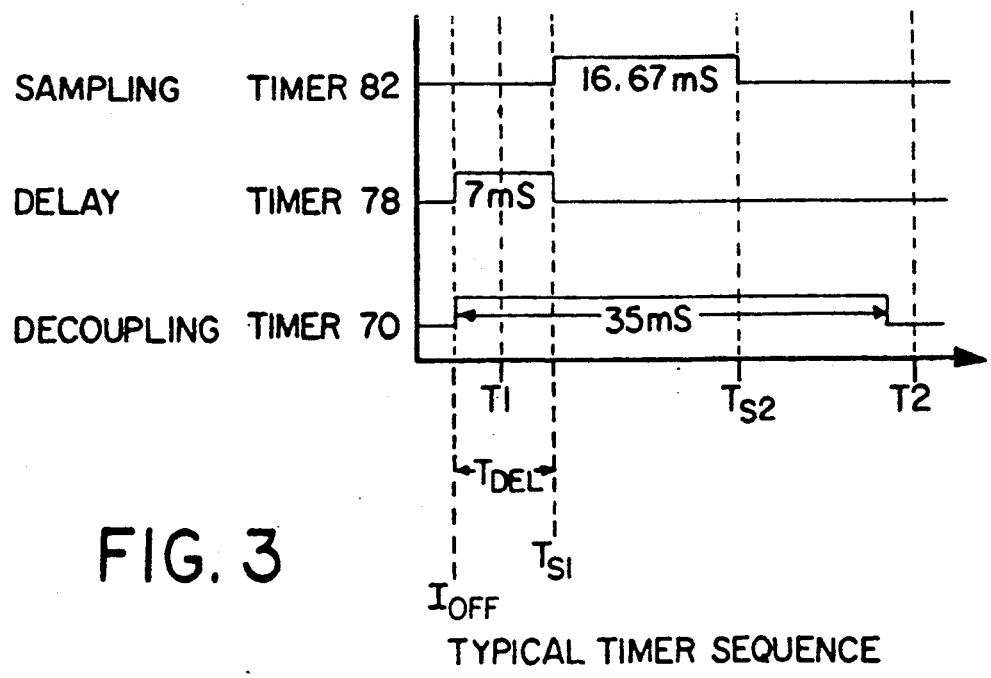
FIG. 3 is a timing diagram showing an exemplary timing sequence in accordance with the present invention for the timers shown in FIG. 2.

Shown in FIG. 3 is a typical timing sequence for the various timers in the system 30 described above. At time $I_{OFF}$, the decoupling timer output 72 goes high causing the coupon 32 to decouple from the metal structure and remain coupled to the test module voltmeter 42 for approximately 35 msec. In addition, the delay timer output 80 goes high at time $I_{OFF}$ and begins 7 msec time delay until time $T_{S1}$, as is described above. The length of the time delay $T_{DEL}$ can be adjusted to compensate for delays in the response time of the solenoid or the like, as will be appreciated.

Upon completion of the 7 msec time delay $T_{DEL}$, the output 84 of the sampling timer goes high. In turn, the sampling timer output 84 enables the S/H circuit 88 for 16.67 msec, thus creating a sampling window $T_{S1}$-$T_{S2}$ within which the voltmeter 42 is used to measure and/or display the sampled polarized potential of the coupon 32.

It will be appreciated in view of the present disclosure that the timer sequence of FIG. 3 is intended to be exemplary; while the illustrated timing sequence might be typical for many applications, it is one of only many possible timing sequences. The delay provided by the delay timer 78, the width of the sampling window $T_{S1}$-$T_{S2}$, and the period of time during which the coupon remains decoupled depends on the particular application. Several techniques may be used to determine the appropriate delay time, sampling window, etc. For example, the respective delays and window widths may be determined empirically. Alternatively, an oscilloscope may be used to determine the shape of the coupon waveform, particularly during decoupling. The operator can use the oscilloscope waveform to determine a satisfactory time delay, sampling window width, decoupling window width, etc.

Based on empirical data, oscilloscope readings, or the like, a library of satisfactory timing sequences for a given application can be formed, thereby eliminating the need to determine such values prior to each measurement. Each respective timer can be adjusted to provide the desired timing response using potentiometers 100-102 as seen in FIG. 2. Suitable timers for use in accordance with the present invention are the commercially available 555 timer manufactured by National Semiconductor and others.

In an alternate embodiment of the present invention, additional circuitry is included in the test module 40 to automatically determine the appropriate delay and window widths. Such circuitry might include a differentiator circuit for sensing when fluctuations in the waveform diminish, thereby identifying when the waveform has reached a relative steady state. The same circuit can be used to determine when the coupon potential has decayed a significant amount due to polarization. In this manner, the window widths and time delays can be computed and implemented automatically using known digital techniques.

Furthermore, while the preferred embodiment is described in the context of using a solenoid activated switch network 43, it will be appreciated that alternate types of switch networks can be applied similarly. For example, switch network 43 might consist solely of solid state, RF, opti-coupled, or fluidic circuitry, or a combination thereof, as opposed to an electro-mechanical solenoid. Alternatively, a primarily mechanical switch may be utilized to provide the desired switching as is exemplified and described more fully below.

Figure 4:
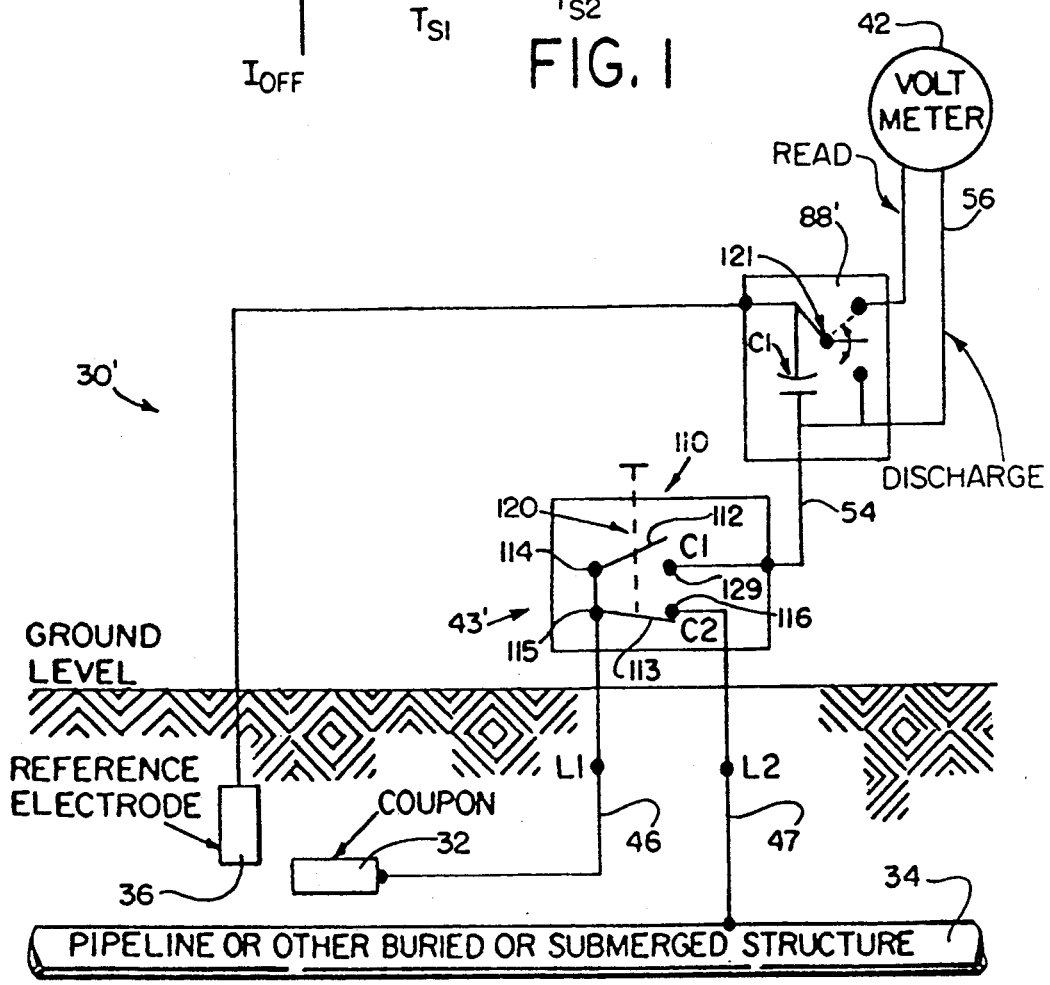
FIG. 4 is a schematic diagram of another embodiment of the cathodic protection monitoring system in accordance with the present invention.

Referring now to FIG. 4, an alternate embodiment of the cathodic protection monitoring system 30' is shown. In this particular embodiment, the switch network 43' utilizes a mechanical plunger switch 110 to provide the desired decoupling and time delay features described above. More specifically, the switch 110 includes contact arms 112 and 113 which pivot about fixed contact pivot points 114, 115, respectively, as shown. The pivot points 114, 115 serve as an electrical connection between the contact arms 112, 113 and cable 46 which is coupled to coupon 32.

As described in greater detail below with respect to FIGS. 5-7, the contact arm 113 is normally closed so as to be in electrical contact with cable 47 such that the coupon 32 is electrically coupled to the metal structure 34. The contact arm 112, on the other hand, is disconnected normally from line 54 which, in turn, is coupled to the input 56 of the voltmeter 42. When the plunger arm 120 is depressed in a downward direction relative to the drawing, the contact arm 113, which is pivotally attached to the plunger arm 120, pivots away and disconnects from contact 116 and cable 47, thereby decoupling the coupon 32 from the metal structure 34. In the meantime, the contact arm 112 begins to pivot into electrical connection with lead 54 such that the coupon 32 becomes coupled to the voltmeter 42 and capacitor C1 charges to the polarized potential of the coupon 32 relative to the reference electrode 36.

After capacitor C1 has been charged, switch 121 is toggled to the READ position (shown in phantom) such that the voltmeter 42 measures the potential across capacitor C1 which represents the polarized potential of the coupon 32. The charge on the capacitor C1 represents the relative potential of the coupon 32 after the desired time delay $T_{DEL}$, as described below. After the polarized potential reading is taken, the toggle switch 121 is thrown in the opposite direction to the DISCHARGE position such that the charge across the capacitor C1 is shorted, and the system is reset. Thereafter, another measurement may be taken using the same approach.

Figure 5:
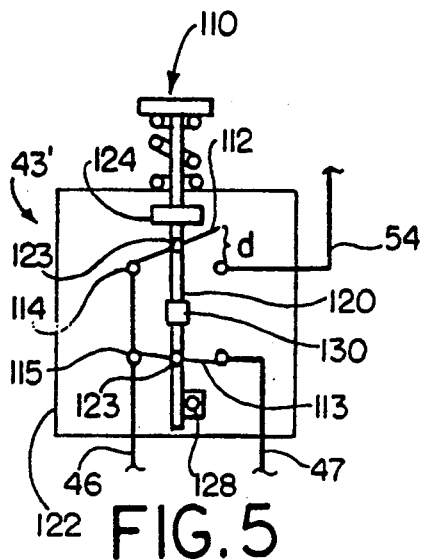
FIGS. 5-7 schematically illustrate the plunger switch of FIG. 4 as used in accordance with the present invention.
Figure 6:
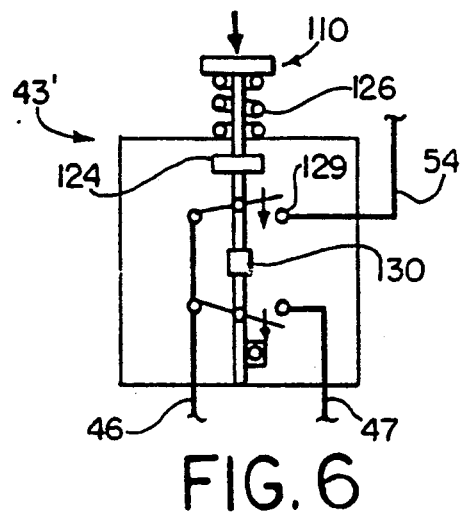
Figure 7:
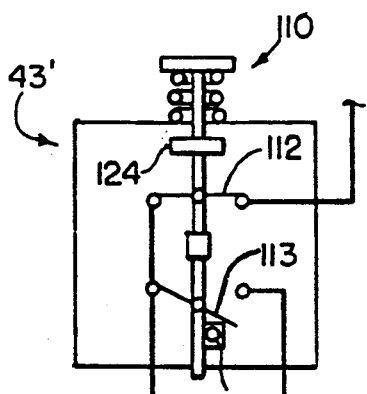

Referring now to FIGS. 5-7, and initially to FIG. 5, the operation of the switch network 43' is described in detail. The switch network 43' includes the plunger switch 110 having a plunger stem 120 which extends through to the interior of the switch network 43' housing 122. As is noted above, the contact arms 112, 113 are mounted to fixed pivot contacts 114, 115, respectively. The approximate center of each contact arm 112, 113 is pivotally attached to the plunger stem 120 at pivot 123 such that the contact arms pivot about their respective pivot contacts as the plunger stem 120 is depressed and released.

The plunger stem 120 is designed to travel through a guide collar 124 as is shown in FIGS. 5-7. The plunger switch 110 includes biasing means such as a spring 126 to bias the plunger to its non-depressed, normally closed position such that the contact arm 113 normally remains in contact with contact 116, thus causing the coupon 32 to remain electrically coupled to the metal structure 34. In addition, the plunger switch 110 includes a governor mechanism 128 which, as described below, governs the rate of travel of the plunger stem 120 in the downward and upward directions relative to the figures.

FIG. 5 shows the switch network 43' in the normal or standby position where the coupon 32 is connected to the metal structure 34 by way of cables 46 and 47 and contact arm 113. When initiating a polarized potential measurement, the operator depresses the plunger stem 120 in a downward fashion, as illustrated in FIG. 6. As soon as the stem 120 is depressed, the contact arm 113 begins to pivot about the pivot contact 115 and pivot 123 and, therefore, disengages contact 116 at time $I_{OFF}$. As the plunger stem 120 continues to travel downward, the contact arm 112 pivots about contact pivot 114 until the contact arm 112 comes into contact with the contact 129 coupled to lead 54. After the contact arm 112 is in connection with lead 54 as illustrated in FIG. 7, the capacitor C1 will charge to the appropriate potential, and the polarized potential measurement can be measured using the voltmeter 42. Once the plunger stem 120 is released, the plunger stem returns to its normally closed position as a result of biasing spring 126.

the duration of the time delay and the width of the sampling window $T_{S1}-T_{S2}$ and decoupling window T1-T2 provided by the switch network 43' can be adjusted as required for a particular application. As will be appreciated, each of these parameters is a function of the distance "d" (FIG. 5) which is the distance the contact arm 112 must travel once the plunger is depressed. In addition, the time delay and respective window widths are a function of the governor 128 setting, the governor 128 controlling the rate at which the contact arm 112 travels the distance d. The delay distance d can be adjusted using an axial adjustment 130 in the plunger stem 120 which controls the spacing of the contact arms 112, 113.

Figure 8:
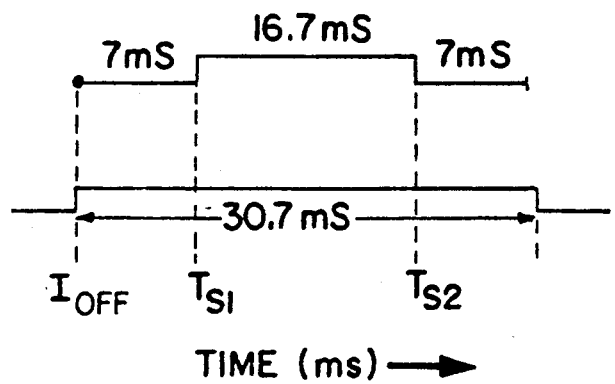
FIG. 8 is a timing diagram showing an exemplary timing sequence for the plunger switch contacts of FIGS. 5-7.

FIG. 8 shows an exemplary timing sequence for the switch network 43' shown in FIGS. 5-7. At time $I_{OFF}$, the plunger stem 120 is initially depressed by the operator. Beginning at time $I_{OFF}$, an approximate 7 msec delay will occur as the contact arm 112 travels the delay distance d as controlled by the governor 128. Assuming the plunger stem 120 is depressed and released shortly thereafter, the sampling window formed by times $T_{S1}$ and $T_{S2}$ represents the time period during which the contact arm 112 is in contact with line 54 causing the capacitor C1 to charge to the relative potential of the coupon 32. At time $T_{S2}$, the contact arm 112 disengages from contact 129 as the released plunger stem 120 travels upward governed by the governor 128. Approximately 7 msec from time $T_{S2}$, contact arm 113 will recouple the coupon 32 to the metal structure.

Various other mechanical, electrical, and electrical-mechanical types of switching networks are possible in order to practice the present invention. The above described embodiments represent but a few of the possible ways of obtaining the desired polarized potential measurement. Therefore, it will be appreciated that it is not intended that the scope of the invention be limited solely to the specific embodiments described herein.

Figure 9:
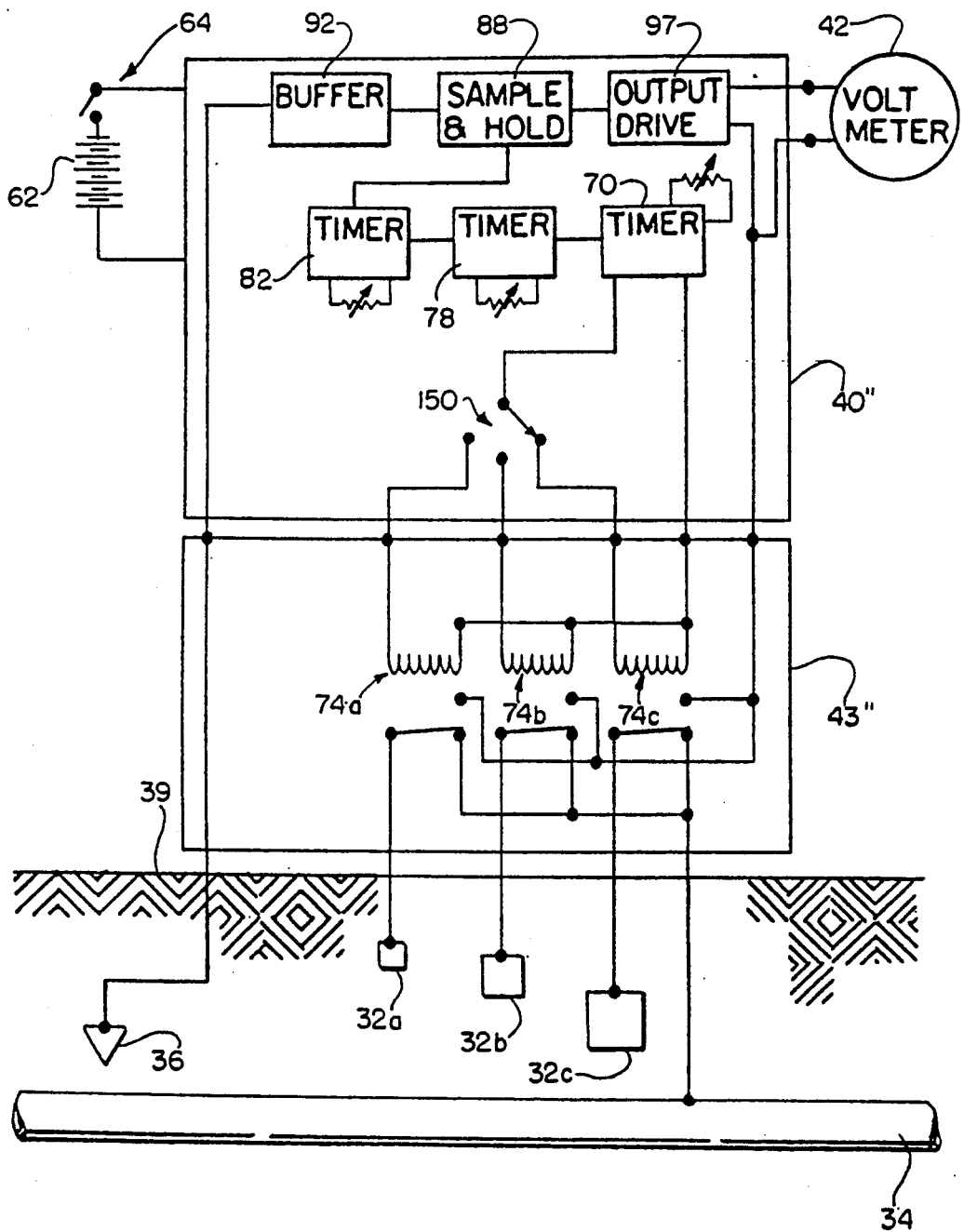
FIG. 9 is a schematic diagram of a multiple coupon embodiment of the cathodic protection monitoring system in accordance with the present invention.

Turning now to FIG. 9, a multiple coupon embodiment of the cathodic protection monitoring system of the present invention is shown. Three coupons 32a-32c are shown, although any number of coupons is possible without departing from the scope of the invention. In the exemplary embodiment, the particular coupon 32a-32c which is used to obtain the polarized potential measurement is determined by selector switch 150. Switch 150 is a rotary switch that controls which solenoid coil 74a-74c is energized. Alternatively, double pole or other type switches may be employed. The operator simply selects which coupon is to be utilized by placing the switch 150 in the appropriate position.

Otherwise, the embodiment shown in FIG. 9 operates in an identical manner to that which is shown and described with respect to FIG. 2. The only difference is that each respective coupon 32a-32c may have different electrical and/or physical characteristics, such as surface area. Alternatively, the multiple coupons can be used in accordance with known multiple coupon techniques such as those disclosed in the above mentioned '565 patent. Furthermore, such a multiple coupon embodiment can be used to obtain a multiple measurement profile of the cathodic protection system without having to move the system 30 to an adjacent test site. Other advantages will be equally apparent in view of the present disclosure.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A method for measuring the polarized potential of a cathodically protected, submerged metal structure substantially IR drop free, said method comprising the steps of:
   placing and coupling a metal coupon at an appropriate position with respect to the structure such that it receives the cathodic protection energy;
   providing a reference electrode positioned appropriately from the coupon and the structure;
   decoupling the coupon from the structure for a first determined length of time;
   coupling said coupon and reference electrode through a voltmeter and measuring the relative voltage thereacross for a second determined length of time, said second determined length of time occurring sometime during said first determined length of time; and
   delaying said measuring step for a third determined length of time, commencing at the same time as said first determined length of time.

2. The method of claim 1, wherein said third determined length of time is no longer than said first determined length of time less said second determined length of time.

3. The method of claim 1, wherein said delay lasts at least until the polarized potential of said coupon has reached a relative steady state.

4. The method of claim 3, wherein said second determined length of time expires prior to the polarized potential of said coupon undergoing substantial decay due to depolarization.

5. The method of claim 1, said measuring step comprising the step of digitally sampling said relative voltage.

6. The method of claim 5, wherein said relative voltage is sampled at a rate which is a whole multiple of the source frequency of a cathodic protection system protecting said structure.

7. The method of claim 5, wherein said relative voltage is sampled at a rate which is a whole multiple of 60 Hz, 50 Hz or other suitable AC frequency.

8. The method of claim 1, wherein said determined lengths of time are predetermined by one or more preset timers.

9. The method of claim 1, wherein said determined lengths of time are determined electronically.

10. The method of claim 9, wherein said determined lengths of time are adjustable.

11. The method of claim 1, wherein said determined lengths of time are determined mechanically by operation of a switch.

12. The method of claim 11, wherein said determined lengths of time are adjustable.

13. The method of claim 11, wherein said switch comprises a double arm mechanically operated switch operative initially to decouple the coupon and structure and then upon said delay, couple the coupon and the reference electrode through said voltmeter.

14. A method as set forth in claim 1 wherein the decoupling of the coupon is obtained by the actuation of a switch at a test site fixed with respect to the structure, said determined lengths of time being provided by a test module which may be connected to the test site to actuate the switch.

15. A method as set forth in claim 14 including a plurality of coupons at each test site, said test site including a switch for each coupon.

16. A method as set forth in claim 15 including the step of selecting the coupon and switch for application of the determined lengths of time.

17. A system for measuring the polarized potential of a cathodically protected buried or submerged metal structure substantially IR drop free, comprising:
means for coupling a metal coupon located at an appropriate position with respect to said structure to the structure such that it receives the cathodic protection energy;
a reference electrode positioned appropriately from the coupon and the structure;
decoupling means for decoupling said coupon from said structure for a first determined length of time;
coupling means for coupling said coupon and reference electrode through a voltmeter and means for measuring the relative voltage thereacross for a second determined length of time, said second determined length of time occurring sometime during said first determined length of time; and
delay means for delaying the measurement of said voltage for a third determined length of time commencing at the same time as said first determined length of time.

18. The system of claim 17, wherein said third determined length of time is no longer than said first determined length of time less said second determined length of time.

19. The system of claim 17, wherein said determined lengths of time are predetermined by one or more preset timers.

20. The system of claim 19, wherein at least one of said one or more preset timers is adjustable.

21. The system of claim 18, each of said decoupling, measuring and delay means comprising a preset timer, and wherein said preset timers predetermine, respectively, said determined lengths of time.

22. The system of claim 21, wherein at least one or more of said preset timers is adjustable.

23. The system of claim 17, wherein said third determined length of time expires at a time when the polarized potential of said coupon has achieved a relative steady state.

24. The system of claim 17, wherein said means for measuring comprises a sample and hold circuit.

25. The system of claim 24, wherein said sample and hold circuit samples the polarized potential of said coupon at a sampling rate which is a whole multiple of the source frequency.

26. The system of claim 24, wherein said sample and hold circuit samples the polarized potential of said coupon at a sampling rate which is a whole multiple of 60 Hz, 50 Hz or other suitable AC frequency.

27. The system of claim 17, further comprising a solenoid-activated switch which, when activated, decouples said coupon from said structure and couples said coupon through to said voltmeter.

28. The system of claim 17, including means determined mechanically by operation of a switch to determine said determined lengths of time.

29. The system of claim 28, wherein said switch comprises a double arm mechanically operated switch operative initially to decouple the coupon and structure and then upon delay, couple the coupon and reference electrode through a voltmeter.

30. The system of claim 29, wherein said switch further comprises a plunger stem to which said double arms are attached.

31. The system of claim 30, said plunger stem comprising an axial adjustment which controls the distance between said attached double arms, and wherein at least one of said determined lengths of time can be adjusted using said axial adjustment.

32. The system of claim 30, wherein said switch further comprises a governor which controls the rate of travel of said plunger stem when depressed during operation.

33. A system as set forth in claim 17 wherein said coupling and decoupling means comprises a switch at a test site.

34. A system as set forth in claim 33 wherein said delay means is provided by a portable test module adapted to be connected to the test site to actuate said switch.

35. A system as set forth in claim 34 including a plurality of coupons at each test site, said test site including a switch for each coupon, said test module including means to select one of the switches and thus the coupon for coupling and decoupling.

* * * * *